United States Patent [19]

McMichael

[11] Patent Number: 6,156,780

[45] Date of Patent: *Dec. 5, 2000

[54] TREATMENT OF FECAL INCONTINENCE

[75] Inventor: John McMichael, Delanson, N.Y.

[73] Assignee: Milkhaus Laboratory, Inc., Delanson, N.Y.

[*] Notice: This patent is subject to a terminal disclaimer.

[21] Appl. No.: 09/132,041

[22] Filed: Aug. 11, 1998

Related U.S. Application Data

[63] Continuation-in-part of application No. 08/731,702, Oct. 17, 1996, Pat. No. 5,877,198.

[51] Int. Cl.$^7$ ...................... A61K 41/415; A61K 31/405
[52] U.S. Cl. ............................................. 514/400; 514/415
[58] Field of Search ..................... 514/400, 415

[56] References Cited

U.S. PATENT DOCUMENTS

| | | | |
|---|---|---|---|
| 4,689,222 | 8/1987 | McMichael | 424/88 |
| 4,692,332 | 9/1987 | McMichael | 424/88 |
| 4,877,610 | 10/1989 | McMichael | 424/88 |
| 4,880,626 | 11/1989 | McMichael | 424/88 |
| 4,966,753 | 10/1990 | McMichael | 424/88 |
| 4,970,071 | 11/1990 | McMichael | 424/88 |
| 5,576,289 | 11/1996 | McMichael | 514/2 |
| 5,610,174 | 3/1997 | Craig et al. | 514/401 |
| 5,877,198 | 3/1999 | McMichael | 514/400 |

FOREIGN PATENT DOCUMENTS

| | | |
|---|---|---|
| WO 87/03487 | 6/1987 | WIPO . |
| WO 89/02220 | 3/1989 | WIPO . |
| WO 91/16819 | 11/1991 | WIPO . |
| WO 95/31996 | 11/1995 | WIPO . |
| WO 96/32138 | 10/1996 | WIPO . |
| WO 98/16225 | 4/1998 | WIPO . |

OTHER PUBLICATIONS

Medline abstract, AN 86137670, Goldberg, M. et al., Jan. 1986.
HCAPLUS abstract, AN 1995:494721, abstract of WO 9506466 A1, Mar. 1995.
Goodman Gilman et al. The Pharmaeological Basis of Therapeutics (6$^{th}$ Ed.), New York: MacMillan, p. 517, 1980.
Castex, N. et al., Gastroenterol. Clin. Biol., vol. 17, pp. 478–84, (France), 1993.
Bueno et al., European Journal of Pharmacology: 192, 263–269 (1991).
Castex et al., Role of Serotonin and Histamine in Colonic Motility and Transit Disturbances Induced by Mast Cell Degranulation: an Experimental Study in the Rat, Laboratoire de Pharmacologie–Toxicologie, INRA, 180, chemin de Tournefeuille, BP 3, F–31931 Toulouse Cedex (translation).
Fargeas et al., J. Pharm. Pharmacol.: 41, 534–540 (1989).
Fargeas et al., Gastroenterology: 102, 157–162 (1992).
Scott, "Mediation of food protein–induced jejunal smooth muscle contraction in sensitized rats," Gastrointestinal Research Group, University of Calgary, Calgary, Alberta T2N 4N1, Canada.
Database HCAPLUS on STN, American Chemical Society, AN 1994:75356, Castex, N. et al., "Role of serotonin and histamine in colonic motility and transit disturbances induced by mast cell degranulation: An experimental study in the rat," Gastroenterol. Clin. Biol., 17(6–7):478–484 (1993) (Abstract).
Physician's Desk Reference®, PDR, 51 Edition 1997, Sansert® methysergide maleate tablets, pp. 2424–2425 (1997).
Gagar et al., "The effects of Bay K 8644 on agonist–induced contractions in guinea pig urinary bladder," Acta Pharm. Jugosl. 41(3):211–216 (1991).
Harrison's Principles of Internal Medicine, Thirteenth Edition, Isselbacher, K.J. et al. (Eds.), pp. 240–241 (1994).
Database HCAPLUS on STN American Chemical Society, AN: 1991:671268; DN: 115: 271268; Gacar, N. et al., "The effects of Bay K 8644 on agonist–induced contractions in guinea pig urinary bladder," Acta Pharm. Jugosl. 41(3):211–216 (1991) (Abstract).
Database HCAPLUS on STN American Chemical Society, AN: 1989:547237; DN: 111: 147237; Yoshinaga, M. et al., "Responsiveness of the isolated and regional preparations of cat vesicourethral system to automatic nervous system–related endogenous agents," Yakuri to Chiryo (JP), 17(5):2049–2055 (1989) (Abstract).

Primary Examiner—Russell Travers
Attorney, Agent, or Firm—Marshall, O'Toole, Gerstein, Murray & Borun

[57] ABSTRACT

The present invention relates to a treatment for patients having fecal incontinence by administering a composition comprising histamine, serotonin or a combination thereof in an amount effective to alleviate symptoms of fecal incontinence.

14 Claims, No Drawings

6,156,780

TREATMENT OF FECAL INCONTINENCE

This application is a continuation-in-part of U.S. patent application Ser. No. 08/731,702 filed Oct. 17, 1996, now U.S. Pat. No. 5,877,198.

FIELD OF THE INVENTION

This invention relates generally to the treatment of incontinence and compositions for use therein. As a further aspect of the invention, methods and compositions for treatment of fecal incontinence are also provided.

BACKGROUND OF THE INVENTION

Urinary incontinence (UI) is often described as either urge incontinence (where urine loss is associated with a sudden or strong desire to void) or stress incontinence (where urine loss is associated with coughing, laughing, or physical exercise). A more general category, mixed incontinence, includes those patients showing both stress and urge symptoms.

Although urinary incontinence is quite prevalent, it is still under-diagnosed and under-reported. The U.S. Department of Health and Human Services estimates that UI affects over 13 million Americans at a cost in excess of $15 billion per year. Many victims of UI do not seek help because of embarrassment or a perception that nothing can be done about their problem. Consequently, the general health and social life of these victims may be significantly compromised for years.

Fecal incontinence is the loss of voluntary control of defecation and can result from injuries or diseases of the spinal cord, injuries to the rectum or anus, senility, diabetes, and extensive inflammatory processes among other causes. In some cases surgery is indicated but treatment generally includes a bowel management program and the use of simple perineal exercises to strengthen the sphincters, perineal muscles and buttocks.

SUMMARY OF THE INVENTION

The present invention relates to methods and compositions for treating patients having urinary and fecal incontinence. In methods according to the invention, compositions comprising histamine, serotonin, or a combination thereof in a pharmaceutically-acceptable vehicle are administered to a patient suffering from urinary or fecal incontinence. Compositions according to the invention comprise at least histamine, serotonin or a combination of the two components.

In a preferred embodiment of the invention, a composition is provided which comprises from about $4\times10^{-1}$ mg to about $4\times10^{-5}$ mg of histamine and from about $2\times10^{-1}$ mg to about $2\times10^{-6}$ mg of serotonin. In another preferred embodiment, a composition is provided which comprises from about $4\times10^{-2}$ mg to about $4\times10^{-4}$ mg of histamine and from about $2\times10^{-2}$ mg to about $2\times10^{-4}$ mg of serotonin. Also in a preferred embodiment, compositions comprising about $1.1\times10^{-3}$ mg of histamine and about $2\times10^{-3}$ mg of serotonin in a total volume of about 0.05 cc (about one drop) are provided.

Methods according to the invention comprise the step of administering a composition comprising histamine, serotonin, or a combination thereof to a patient suffering from urinary or fecal incontinence. In a preferred method of the invention, compositions according to the invention are provided in a dose of about 0.05 cc. Preferably, from about 1 to about 3 doses are administered daily.

The precise amount of such compositions may vary depending upon, inter alia, the severity of a patient's incontinence and a patient's response to treatment, but may readily be determined by observation of the patient's response to treatment.

DETAILED DESCRIPTION OF THE INVENTION

The invention consists of the use of histamine, serotonin or a combination thereof to successfully treat urinary or fecal incontinence.

The histamine used according to the methods of the invention is preferably in the form of a soluble salt such as histamine phosphate. The preferred concentration of histamine base in each dose of the invention is generally within the range of about $4\times10^{-1}$ mg to about $4\times10^{-5}$ mg. More preferably, the concentration of histamine base in each dose of the invention is generally within the range of about $4\times10^{-2}$ mg to about $4\times10^{-4}$ mg, and most preferably about $1.1\times10^{-3}$ mg, of histamine per dose.

The preferred concentration of the serotonin in each dose of the invention contains from about 0.2 mg to about $2\times10^{-6}$ mg of serotonin (5-hydroxytryptamine). More preferably, the concentration of serotonin is generally within the range of about $2\times10^{-2}$ mg to about $2\times10^{-4}$ mg, and most preferably about $2\times10^{-3}$ mg, of serotonin.

Methods for administering the present invention to a patient suffering from urinary or fecal incontinence vary and may include, inter alia, administration subcutaneously, interperitoneally, intravenously, intramuscularly, or sublingually, with sublingual administration being particularly preferred.

According to the present invention, histamine and serotonin may be combined in a single composition or may be administered individually. Generally, a patient begins treatment by sublingually administering one drop three times daily, with each drop being equivalent to about 0.05 cc. The number of drops may vary daily.

Provided below are case histories of patients diagnosed with urinary or fecal incontinence. The case histories provide evidence of the effectiveness of the treatment methods and compositions as described herein. These patients were treated with methods according to the invention comprising the step of administering a composition comprising histamine, serotonin, or a combination thereof to a patient suffering from urinary or fecal incontinence. The histamine used in these trials was obtained from Allermed Laboratories. The serotonin used was Sigma's 5-hydroxytryptamine. All the patients showed improvement. Although the invention was administered sublingually in the cases described below, it is expected that other routes of administration would be equally efficacious. Table I summarizes the treatment of these patients.

Evaluation of the progress of patients diagnosed with urinary incontinence is determined by the patients themselves with a Visual Analog Scale (VAS) to determine their degree of affliction before and after treatment with the invention. These patients started with a VAS score of 10 at the initiation of the trial. These patients were also all treated by the same physician. As set forth in the examples and Table I, the patients disclosed in Examples 1–6 initially participated in a study using CP-A, a composition containing about 0.05 cc (about 1 drop) of a 1:25 dilution of influenza virus vaccine (Fluvirin™, manufactured and released by Evans Medical Limited), about $1.1\times10^{-3}$ mg of histamine, and about $2\times10^{-3}$ mg of serotonin. The diluent used was a phenylated saline.

EXAMPLE 1

(Urinary Incontinence)

An 82 year old female with a history of a 3–4+ cystocele for six years was presented for treatment. She complained of severe urinary incontinence. She wet 3 to 4 pads per day. Without pads, urine would run down her legs. On Day 0, she was treated by sublingual administration of one drop three times a day of CP-A (a composition according to the invention comprising about 0.05 cc of a 1:25 dilution of influenza virus vaccine, about $1.1 \times 10^{-3}$ mg of histamine, and about $2 \times 10^{-3}$ mg of serotonin). Within two days, she had minimal leaking and felt tighter. By Day 27, her pads were dry. She experienced no leaking and her drops were decreased to one drop per day. Her score decreased from a 10 (pre-study) to 0 (no symptoms). On Day 101, her treatment was changed to sublingual administration of one drop per day of HS (a composition according to the invention containing about $1.1 \times 10^{-3}$ mg of histamine and about $2 \times 10^{-3}$ mg of serotonin). On Day 122, her urgency returned but she had no leakage. On Day 150, she felt she improved to a score of 2. (She was a score of 0 on CP-A). On Day 150, the drops of HS were increased to three a day. On Day 160, she felt better and her score improved to a 1. Her remaining symptom was urgency. On Day 160, the patient's treatment was changed to administration of 1 drop a day of H (a composition containing about $1.1 \times 10^{-3}$ mg of histamine). Her score was a 0. On Day 217, her treatment was changed to administration of 1 drop of S (a composition containing about $2 \times 10^{-3}$ mg of serotonin) per day. On Day 238, the patient felt "too tight" on 1 drop per day and was decreased to 1 drop every 2 days. Her final score was a 0.

EXAMPLE 2

(Urinary Incontinence)

A 51 year old female who complained of a 5–6 year history of incontinence with sneezing, running, walking too fast, and jumping rope was presented for treatment. She had a 1+ cystocele. On Day 0, she was treated by sublingual administration of one drop three times a day of the CP-A composition of Example 1. Her score was a 10. By Day 16, she experienced no leakage with sneezing (score 0), minimal leaking with walling (score 1), and no leaking with jumping rope (score 0). She did not test herself while running. By Day 48, all of her symptoms were resolved except for a small amount of leakage that she experienced while sneezing. Furthermore, on Day 48, she noticed that the chronic bursitis pain that she had endured for two years improved to a score of 4 in severity from a pre-study score of 7 (10 being the most severe). She was able to raise her arm better. On Day 48, her drops were decreased to one a day. On Day 62, she reported more control of her bladder control muscles. She also noted improvement in her legs which had ached in bed for years (a score of 3 decreased from 10). On Day 72, her treatment was changed to one drop per day of the HS composition of Example 1. On Day 94, her leaking returned. The drops were increased to three per day. Her score was 4. (She was a score of 0 on CP-A). On Day 108, she experienced leaking less often. Her drops were decreased to one drop twice a day for a week then to one drop a day. By Day 125, her score was a 1. On Day 149, she was still a 1. (Her score was a 0 on CP-A). She occasionally lost urine while bending over. On Day 148, the patient's treatment was changed to 1 drop a day of the S composition of Example 1. The drops of S were increased to 3 a day. Her score was a 1. On Day 196, the treatment was changed to 3 drops a day of the H composition of Example 1. Her final score was a 2.

EXAMPLE 3

(Urinary Incontinence)

A 59 year old female with a 6–8 year history of nocturia once a night, incontinence with sneezing, coughing, running, and dribbling with urgency 5–6 times per week was presented for treatment. On Day 0, she was treated by sublingual administration of one drop three times a day of the CP-A composition of Example 1. Her score was a 10 pre-study. By Day 13, she had no urgency riding in a car from work, had more control and was not up at night. Her score improved to a 5. Her treatment was increased to six drops per day of CP-A. By Day 32, she was again up at night and her urgency returned. Her score increased to 10. Her drops were decreased back to three drops per day. On Day 38, her score had dropped to a 5, and her drops were decreased to two drops per day. On Day 41, she had no nocturia and urgency was improved (score 3–4). By Day 58, she had no incontinence with cough (score 0), no nocturia, and her urgency was a score of 2. Her drops were decreased to one drop per day. Her score was a 1 by Day 65. On Day 65, her treatment was changed to sublingual administration of one drop per day of the HS composition of Example 1. On Day 90, her score was a 5. By Day 122, her score improved to a 0. She felt better than when she was treated with CP-A. Her main symptoms were dribbling and urinary incontinence. She was kept on one drop per day of HS until Day 146, when the patient's treatment was changed to 1 drop a day of the H composition of Example 1. Her score was a 0. On Day 212, her treatment was changed to 1 drop a day of the S composition of Example 1. Her score was a 1.

EXAMPLE 4

(Urinary Incontinence)

A 34 year old female with a nine year history of stress incontinence while coughing, laughing, and running was presented for treatment. She needed to wear pads. On Day 0, she was treated by sublingual administration of one drop three times a day of the CP-A composition of Example 1. She experienced no change. On Day 45, her drops were increased to six per day. By Day 67, she experienced some good days, having no leakage, but experienced no change on other days. On Day 73, her drops were decreased to two per day. By Day 87, she felt her symptoms overall had improved to a score of 5. On Day 87, her treatment was changed to 1 drop twice a day of the HS composition of Example 1. On Day 101, she was leaking less often. By Day 133, she improved more and the drops were decreased to 1 drop per day. On Day 156, she stated she dribbled once every 3 to 4 coughing spells where she had been dribbling with every cough previously. Some days she experienced no leaking at all. Her score was a 2. (She was a 5 on CP-A). On Day 157, the patient's treatment was changed to 1 drop a day of the S composition of Example 1. Her score was a 2. On Day 213, her treatment was again changed to 1 drop a day of the H composition of Example 1. Her final score was a 1.

EXAMPLE 5

(Urinary Incontinence)

A 58 year old female with a three year history of voiding every two hours, wetting herself with least movement, and incontinence with sneezing and coughing was presented for treatment. She used pads. On Day 0, she was treated by sublingual administration of one drop three times a day of the CP-A composition of Example 1. By Day 33, her pre-study score decreased to a 5 with motion and to a 3 with walking. Her frequency also decreased. Her drops were decreased to one drop twice a day. By Day 48, her leakage with walking dropped to a score of 1, with motion 2, with coughing 3, and with sneezing 2. Her final score overall was a 2. On Day 48, her treatment was changed to one drop twice a day of the HS composition of Example 1. On Day 66, she experienced no leaking while walking vigorously and did not use pads. On Day 119, she was a score of 1. (She was a score of 2 on CP-A). On Day 155, the patient's treatment was changed to 1 drop a day of the S composition of Example 1. Her score was a 1. On Day 198, the patient's treatment was changed to 1 drop a day of the H composition of Example 1. Her score remained a 1.

EXAMPLE 6

(Urinary Incontinence)

A 39-year old female with a 10 year history of stress incontinence with running and jumping, and of urgency incontinence was presented for treatment. She dribbled while walking into the bathroom. Cold air increased urgency. On Day 0, she was treated by sublingual administration of one drop three times a day of the CP-A composition of Example 1. By Day 12, her symptoms improved to a 3–4. She was out of drops from Day 30–Day 38, and her score returned to a 10. Her drops were increased to six per day. She experienced no changes. On Day 44, she returned to three drops per day. By Day 50, she experienced no change. On Day 58, she developed an acute urinary tract infection. On Day 64, her treatment with CP-A was stopped when she felt she was not emptying her bladder well. Leakage returned while running. On Day 101, she was again treated with the CP-A composition of Example 1. This patient was kept on CP-A because the previous results were possibly affected by a cystitis. She experienced no change. On Day 128, her drops were decreased to one drop twice a day. She developed severe migraine headaches and her treatment was ceased on Day 137. She had experienced migraines prior to the use of CP-A. On Day 311, she tried treatment again using the CP-A composition of Example 1, without phenol, and experienced no change. As of Day 346, she experienced no change, thus these drops were discontinued.

EXAMPLE 7

(Urinary Incontinence)

A 66 year old with a history of urinary frequency, urgency, and incontinence with coughing was presented for treatment according to the invention. Used panty liners for protection. Onset two years. The patient was treated with the HS composition of Example 1 on Day 0 at one drop three times a day. On Day 10, the patient had no dribbling with cough, urgency was unchanged, frequency was less, and the only leakage occurred with severe urgency. Her VAS score was 2 on a 0–10 scale (10 pretreatment). The HS drops were decreased to two per day on Day 10. On Day 17, the patient had no dribbling and less frequency. Urgency was present. No dribbling with cough. On Day 24, the drops were decreased to one per day. On Day 65, her score was a 3 on one drop per day. On Day 65, the patient's treatment was changed to one drop per day of the H composition of Example 1. Some leakage occurred and the drops were increased to three per day. By Day 134, the patient was doing better with a score of 1–2 on treatment according to the invention using H, three drops per day.

EXAMPLE 8

(Urinary Incontinence)

A 71 year old with nocturia twice nightly, urinary frequency, urgency, and occasional dribbling especially with stooping over was presented for treatment according to the invention. Onset of more than 10 years. On Day 0, the patient was treated with three drops per day of the HS composition of Example 1. By Day 15, dribbling was less, but otherwise no major change. The drops were decreased to twice a day. By Day 23, the patient was not leaking as much while stooping. VAS score was still a 9. By Day 38, the dribbling continued to improve. The bladder did not feel like it was dropped. Nocturia was 1–2/night. By Day 59, nocturia decreased to once at night. Less frequency. Her VAS score was 5. The patient incidentally noticed less arthritic pain, constipation was better, and feet/hands were warmer. She was decreased to one drop per day. Score by Day 91 remained a 5. The patient's treatment was changed to one drop per day of the S composition of Example 1 on Day 91. By Day 105, she stated within two days of going from HS to one drop a day of S, her nocturia worsened (2 per night) and leakage was worse (score 7). Drops were increased to three per day. By Day 118 her score was again 5. By Day 153, her score was 3 (on 2 drops per day). By Day 172, she was on one drop per day of S and scored about a 3. Unfortunately, arthritic pain in her feet and wrists and cold in her extremities returned.

EXAMPLE 9

(Urinary Incontinence)

A 39 year old with urgency and dribbling presented for treatment according to the invention. Onset of about 3 years. On Day 0, the patient was treated with three drops per day of the HS composition of Example 1. By Day 4, her leakage (accidents) decreased from daily to once over four days. Her VAS score decreased to a 3. On Day 7, her drops were decreased to two drops per day. She felt better overall. Within the next two weeks, her drops of HS were decreased to one per day. She felt best on two drops per day. She had no leakage with cough, accidents were about one a week, and she felt tighter. On HS, the patient experienced 70% improvement within four days. Her best response was two drops per day. When she ran out of drops, symptoms recurred within two weeks.

EXAMPLE 10

(Fecal Incontinence)

According to a further aspect of the present invention it has been found that administration of the formulation used for treatment of urinary incontinence is also useful for the treatment of fecal incontinence. Specifically, a 68 year old female with multiple year history of fecal incontinence which was experienced up to four times per day was treated by sublingual administration with a composition according to the invention containing about $1.1 \times 10^{-3}$ mg of histamine and about $2 \times 10^{-3}$ mg of serotonin, (HS drops) at rate of one drop three times daily. After one week of treatment the subject reported no uncontrolled soiling. The subject then reported feeling constipated and used a fiber laxative which resulted in a normal bowel movement. Frequency of administration of the histamine and serotonin composition was then reduced to one drop every other day or one drop as needed with no occurrences of fecal incontinence and no feeling of constipation.

Numerous modifications and variations of the above-described invention are expected to occur to those of skill in the art. Accordingly, only such limitations as appear in the appended claims should be placed thereon.

TABLE I

SUMMARY OF TREATMENT OF URINARY INCONTINENCE

| | CP-A | | | HS | | | H | | | S | | |
|---|---|---|---|---|---|---|---|---|---|---|---|---|
| Patient | Date Began | Final Score | Drops Per Day | Date Began | Final Score | Drops Per Day | Date Began | Final Score | Drops Per Day | Date Began | Final Score | Drops Per Day |
| Example 1 | Day 0 | 0 | 1 | Day 101 | 1 | 3 | Day 160 | 0 | 1 | Day 217 | 0 | 1 drop every 2 days |
| Example 2 | Day 0 | 0 | 1 | Day 72 | 1 | 1 | Day 196 | 2 | 3 | Day 148 | 1 | 3 |
| Example 3 | Day 0 | 1 | 1 | Day 65 | 0 | 1 | Day 146 | 0 | 1 | Day 212 | 1 | 1 |
| Example 4 | Day 0 | 5 | 2 | Day 87 | 2 | 1 | Day 213 | 1 | 1 | Day 157 | 2 | 1 |
| Example 5 | Day 0 | 2 | 2 | Day 48 | 1 | 1 | Day 198 | 1 | 1 | Day 155 | 1 | 1 |
| Example 6 | Day 0 | | | | | | | | | | | |
| Example 7 | | | | Day 0 | 3 | 1 | Day 65 | 1–2 | 3 | | | |
| Example 8 | | | | Day 0 | 5 | 1 | | | | Day 91 | 3 | 1 |
| Example 9 | | | | Day 0 | 3 | 1 | | | | | | |

What is claimed is:

1. A method for treating a patient having fecal incontinence, comprising the step of:
   administering a composition comprising a member selected from the group consisting of histamine and serotonin in an amount effective to alleviate symptoms of fecal incontinence.

2. The method of claim 1, wherein said composition comprises from about $4\times10^{-1}$ mg to about $4\times10^{-5}$ mg of histamine.

3. The method of claim 1, wherein said composition comprises from about $4\times10^{-2}$ mg to about $4\times10^{-4}$ mg of histamine.

4. The method of claim 1, wherein said composition comprises about $1.1\times10^{-3}$ mg of histamine.

5. The method of claim 1, wherein the histamine used is in the form of a soluble salt.

6. The method of claim 1, wherein said composition comprises from about $2\times10^{-1}$ to about $2\times10^{-6}$ mg of serotonin.

7. The method of claim 1, wherein said composition comprises $2\times10^{-2}$ mg to about $2\times10^{-4}$ mg of serotonin.

8. The method of claim 1, wherein said composition comprises about $2\times10^{-3}$ mg of serotonin.

9. The method of claim 1, wherein said composition is administered to a patient in a single dose of about 0.05 cc in a pharmaceutically acceptable carrier.

10. The method of claim 9, wherein multiple daily doses of said composition are administered to the patient.

11. The method of claim 9, wherein the composition is administered to a patient sublingually.

12. The method of claim 1, wherein said composition comprises from about $4\times10^{-1}$ mg to about $4\times10^{-5}$ mg of histamine and from about $2\times10^{-1}$ to about $2\times10^{-6}$ mg of serotonin.

13. The method of claim 1, wherein said composition comprises from about $4\times10^{-2}$ mg to about $4\times10^{-4}$ mg of histamine and from about $2\times10^{-2}$ to about $2\times10^{-4}$ mg of serotonin.

14. The method of claim 1, wherein said composition comprises about $1.1\times10^{-3}$ mg of histamine and about $2\times10^{-3}$ mg of serotonin.

* * * * *